United States Patent [19]
Bays

[11] Patent Number: 6,010,477
[45] Date of Patent: Jan. 4, 2000

[54] SURGICAL BLADES ASSEMBLY

[75] Inventor: F. Barry Bays, Clearwater, Fla.

[73] Assignee: Xomed Surgical Products, Inc., Jacksonville, Fla.

[21] Appl. No.: 09/005,012

[22] Filed: Jan. 9, 1998

Related U.S. Application Data

[60] Division of application No. 08/775,147, Dec. 31, 1996, abandoned, which is a continuation-in-part of application No. 08/719,130, Sep. 24, 1996, abandoned.

[51] Int. Cl.$^7$ .................................................. A61B 17/20
[52] U.S. Cl. ............................ 604/22; 606/170; 606/180
[58] Field of Search ................................ 604/22, 35, 43; 606/167, 170, 180

[56] References Cited

U.S. PATENT DOCUMENTS

| Re. 34,556 | 3/1994 | Sjostrom et al. . |
|---|---|---|
| 1,630,239 | 5/1927 | Binkley et al. . |
| 3,618,611 | 11/1971 | Urban . |
| 3,657,818 | 4/1972 | Garnier . |
| 3,882,872 | 5/1975 | Douvas et al. . |

(List continued on next page.)

FOREIGN PATENT DOCUMENTS

| 0310285 | 9/1988 | European Pat. Off. . |
|---|---|---|
| 2362157 | 12/1973 | Germany . |
| 2093353 | 2/1982 | United Kingdom . |

OTHER PUBLICATIONS

"Advanced Arthroscopic Surgical System Manual", Dyonics, Inc., 160 Dascomb Road, Andover, MA 01810, Jan. 23, 1985.

"Beyond all others Advanced Arthroscopic Surgical System from Dyonics", Dyonics, Inc., 160 Dascomb Road, Andover, MA 01810.

Intra–Arc™ Drive System, Concept Incorporated, 12707 U.S. 19 South, Clearwater, Florida 33546.

"The Elite Arthroscopy Power System", Stryker Endoscopy.

"Total Arthroscopy System", Richard Wolf Medical Instruments Corp., 7046 Lyndon Avenue, Rosemont, IL 60018.

"Introducing The Hall® Arthrotome® System High Speed Handpiece" The Hall® Arthrotome™ System Instruction Manual.

"The Stryker Microelectric Arthroplasty System", Stryker, 420 Alcott Street., Kalamazoo, MI 49001, USA.

*Primary Examiner*—Wynn Wood Coggins
*Assistant Examiner*—Eric Kline

[57] ABSTRACT

A powered handpiece for driving a surgical blade to cut anatomical tissue includes a reusable handpiece body having a distal end for being coupled with a surgical blade, a drive shaft in the handpiece body for rotatably driving the surgical blade, a motor assembly for being installed in the handpiece body to rotatably drive the drive shaft and a suction channel in the handpiece body including a portion extending through the drive shaft parallel to a longitudinal axis of the motor assembly for evacuating anatomical tissue cut by the blade from the handpiece body for external collection. The surgical blade is for use with the powered handpiece and carries a sealing arrangement facilitating irrigation and suction. The handpiece body is capable of being sterilized to medical standards prior to each use. The motor assembly, which is non-sterile, is removable from the handpiece body prior to sterilization of the handpiece body and is reinstallable in the handpiece body subsequent to sterilization of the handpiece body without contaminating the sterilized handpiece body. An installation device includes a reusable funnel for being disposed over the handpiece body and through which the motor assembly is inserted for installation in the handpiece body. An electric cord assembly for being coupled between the handpiece and a power console includes a plug for being plugged into the motor assembly after the motor assembly has been installed in the handpiece body and a locking ring on the plug for selectively, releasably, lockingly engaging the handpiece body to secure the motor assembly in the handpiece body.

12 Claims, 7 Drawing Sheets

U.S. PATENT DOCUMENTS

| | | |
|---|---|---|
| 3,937,222 | 2/1976 | Banko . |
| 4,167,943 | 9/1979 | Banko . |
| 4,200,106 | 4/1980 | Douvas et al. . |
| 4,203,444 | 5/1980 | Bonnell et al. . |
| 4,274,414 | 6/1981 | Johnson et al. . |
| 4,314,560 | 2/1982 | Helfgott et al. . |
| 4,320,761 | 3/1982 | Haddad . |
| 4,445,509 | 5/1984 | Auth . |
| 4,517,977 | 5/1985 | Frost . |
| 4,522,206 | 6/1985 | Whipple et al. . |
| 4,577,629 | 3/1986 | Martinez . |
| 4,601,290 | 7/1986 | Effron et al. . |
| 4,649,919 | 3/1987 | Thimsen et al. . |
| 4,705,038 | 11/1987 | Sjostrom et al. . |
| 4,729,763 | 3/1988 | Henrie . |
| 4,752,444 | 6/1988 | Bowen et al. . |
| 4,811,734 | 3/1989 | McGurk-Burleson et al. . |
| 4,815,462 | 3/1989 | Clark . |
| 4,834,729 | 5/1989 | Sjostrom . |
| 4,998,527 | 3/1991 | Meyer . |
| 5,112,299 | 5/1992 | Pascaloff ................... 604/22 |
| 5,152,744 | 10/1992 | Krause et al. . |
| 5,792,167 | 8/1998 | Kablik et al. ........................ 606/180 |

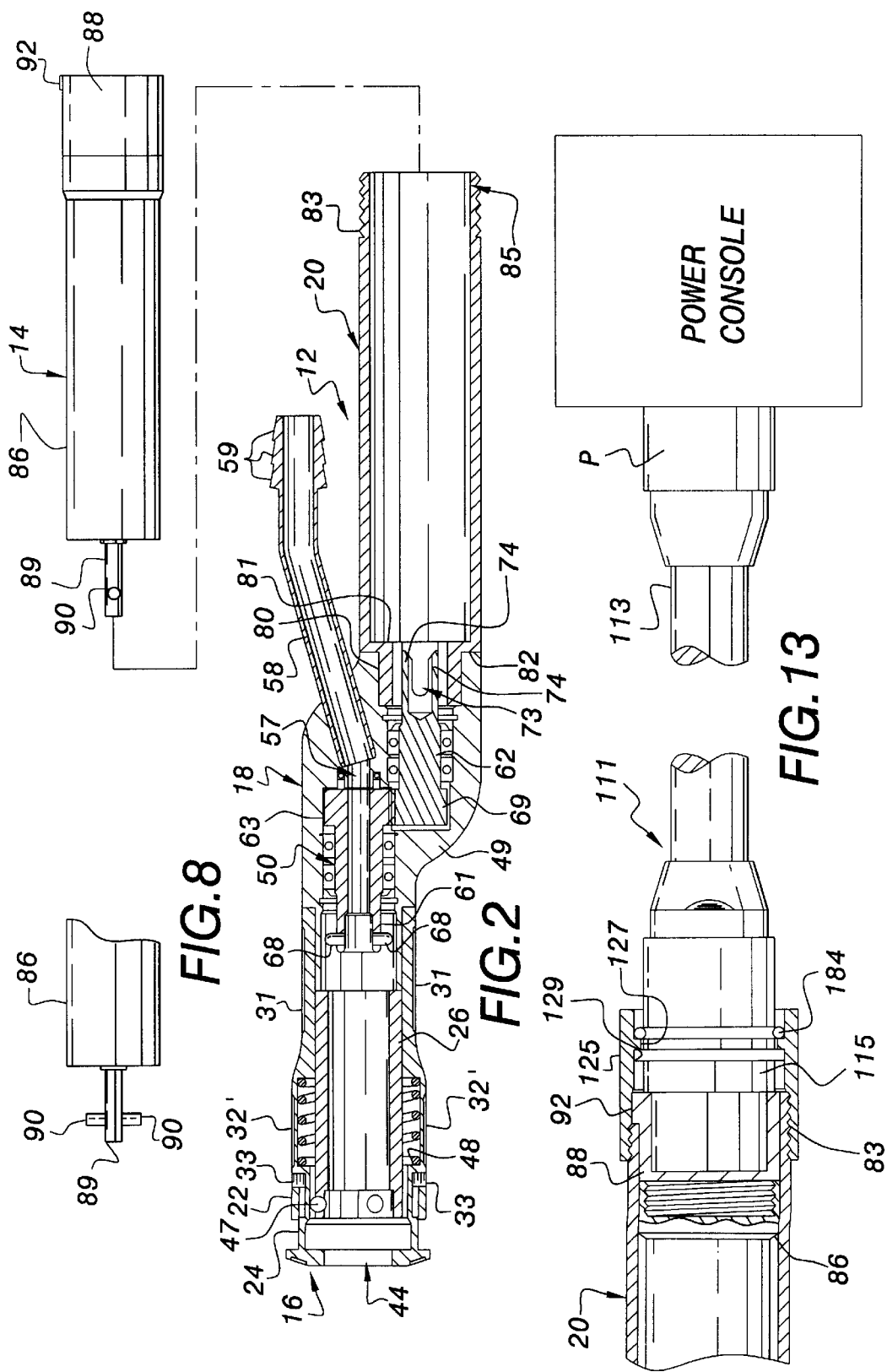

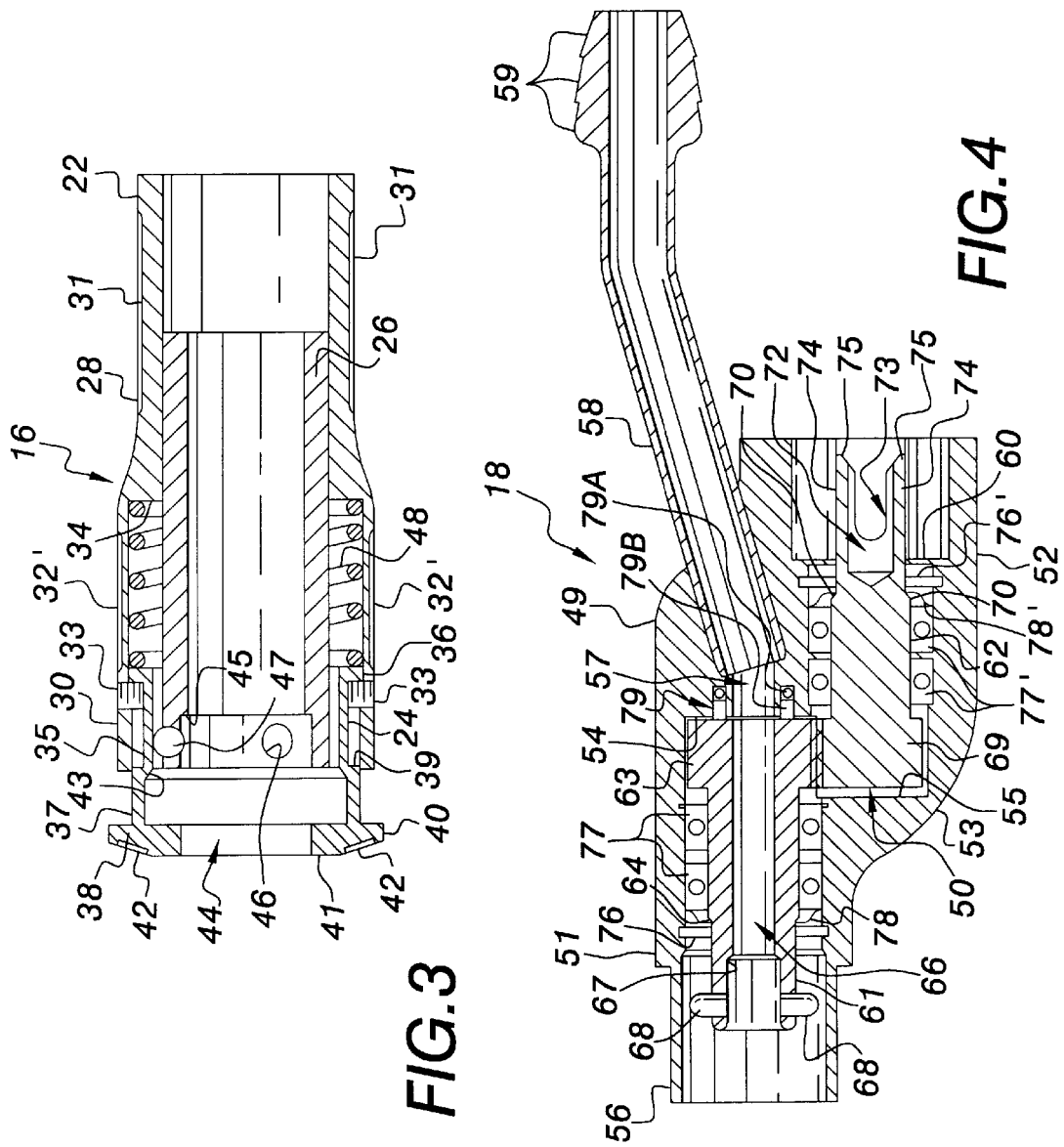

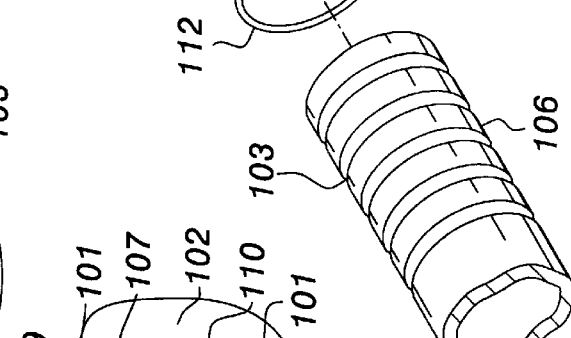
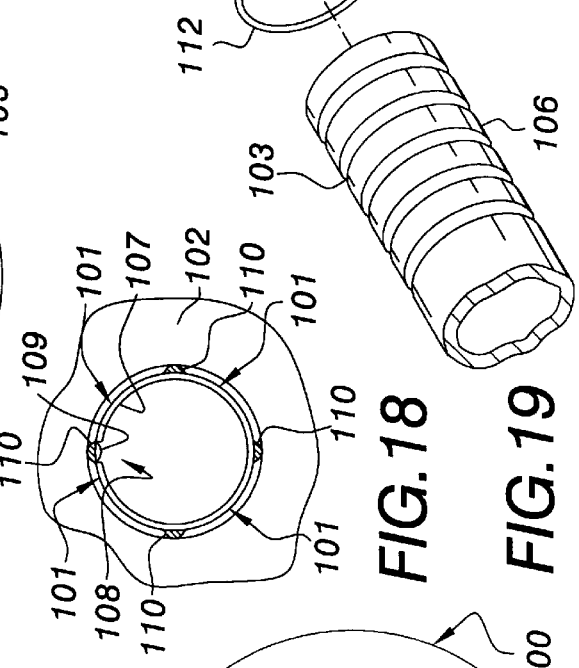
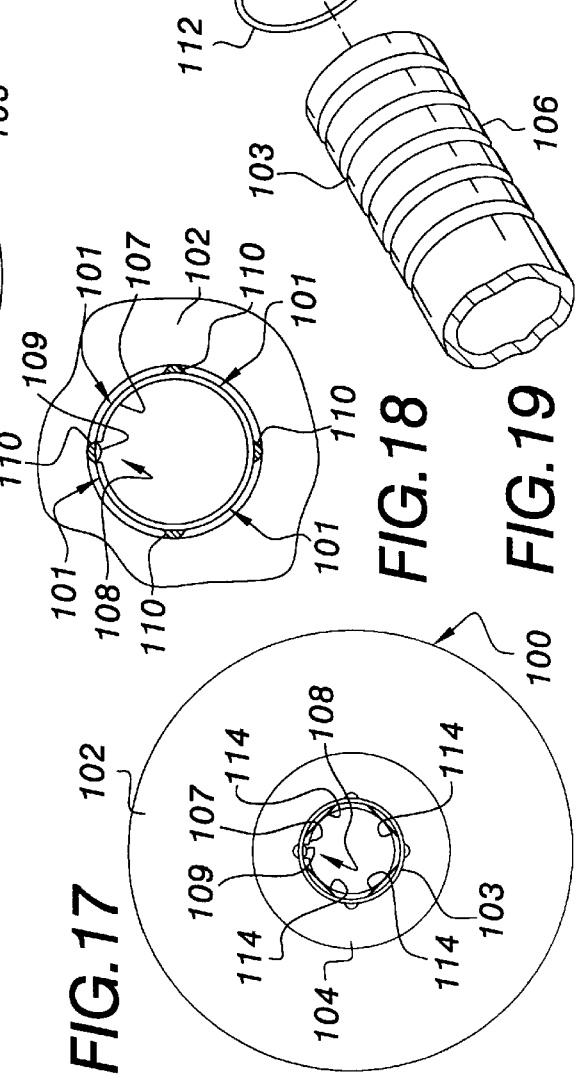
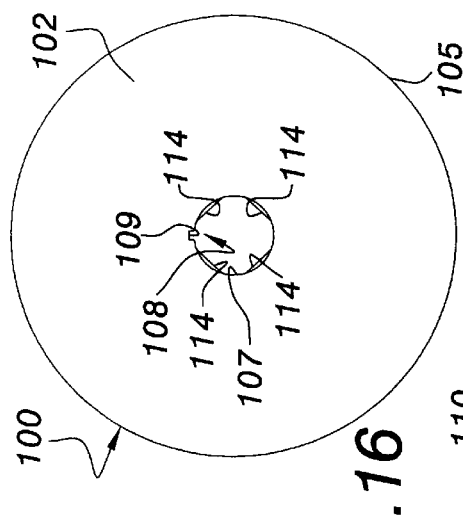
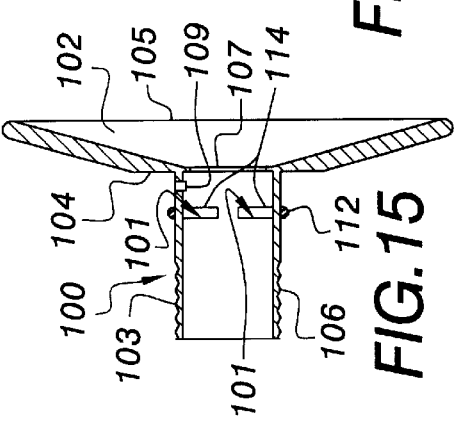
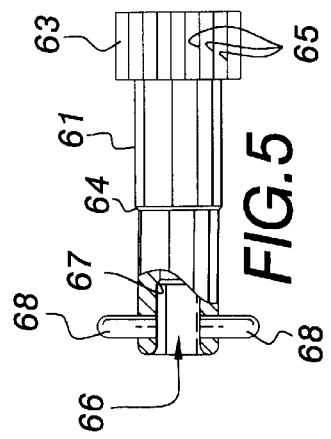
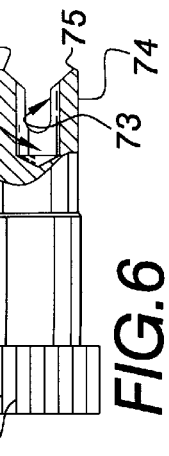

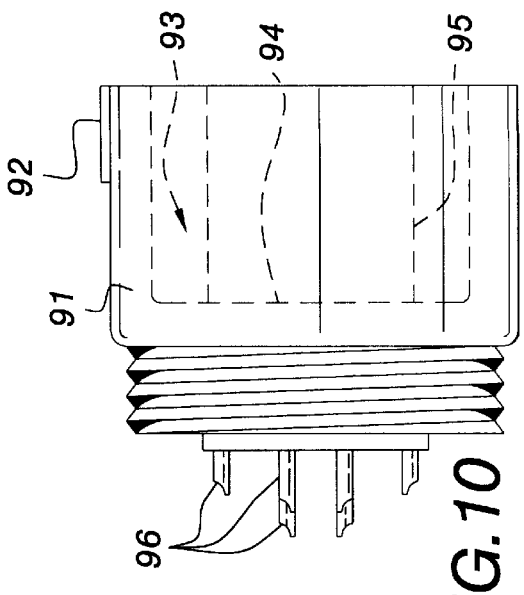
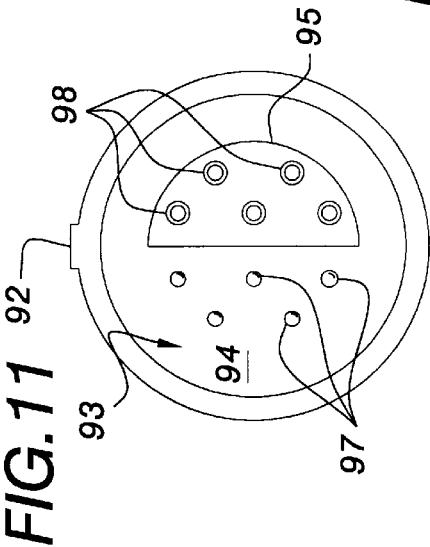
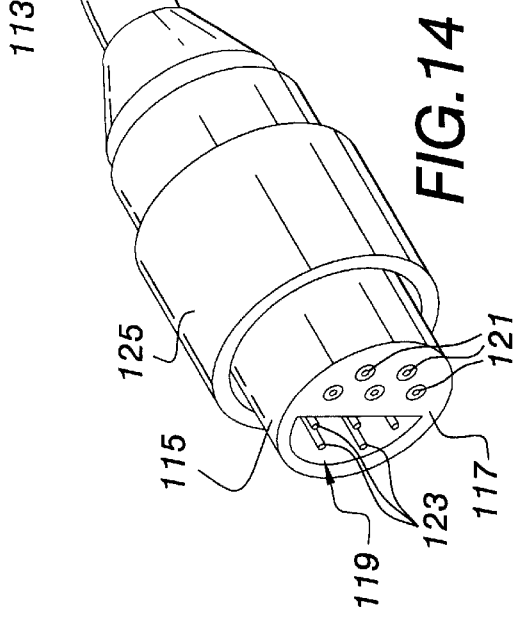
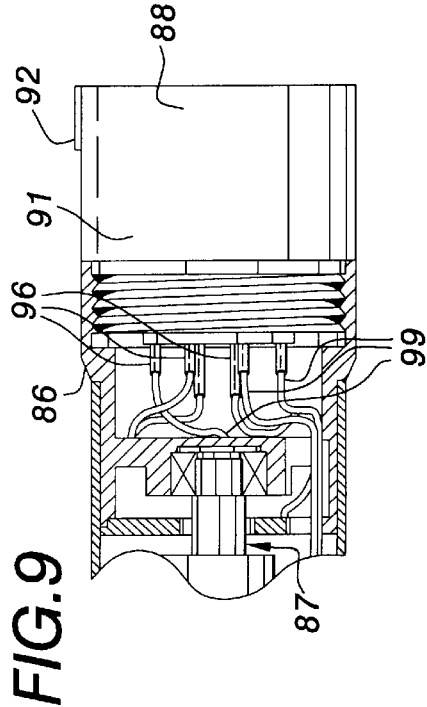
FIG.9 FIG.10 FIG.11 FIG.12 FIG.14

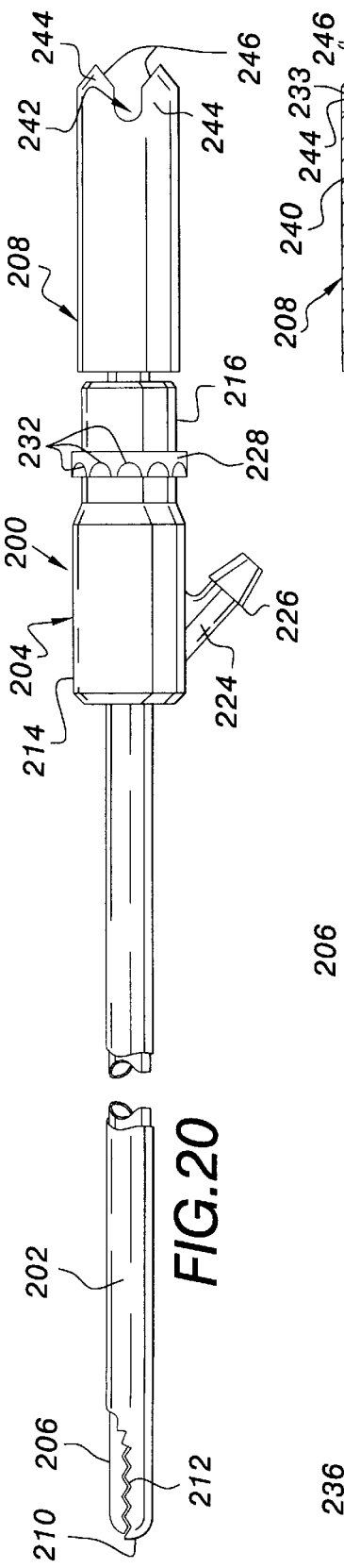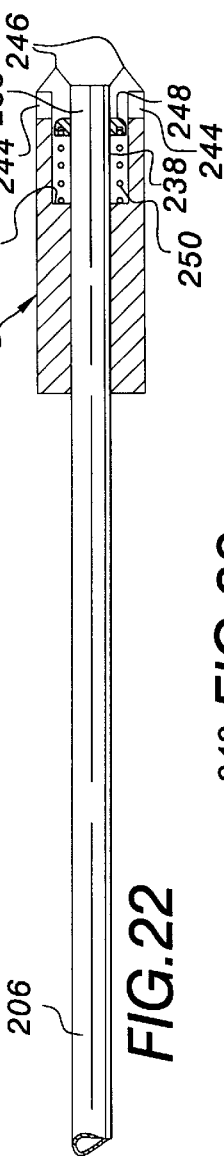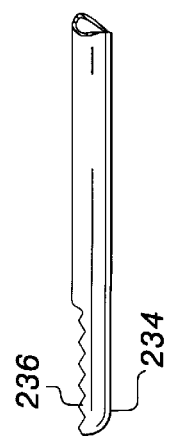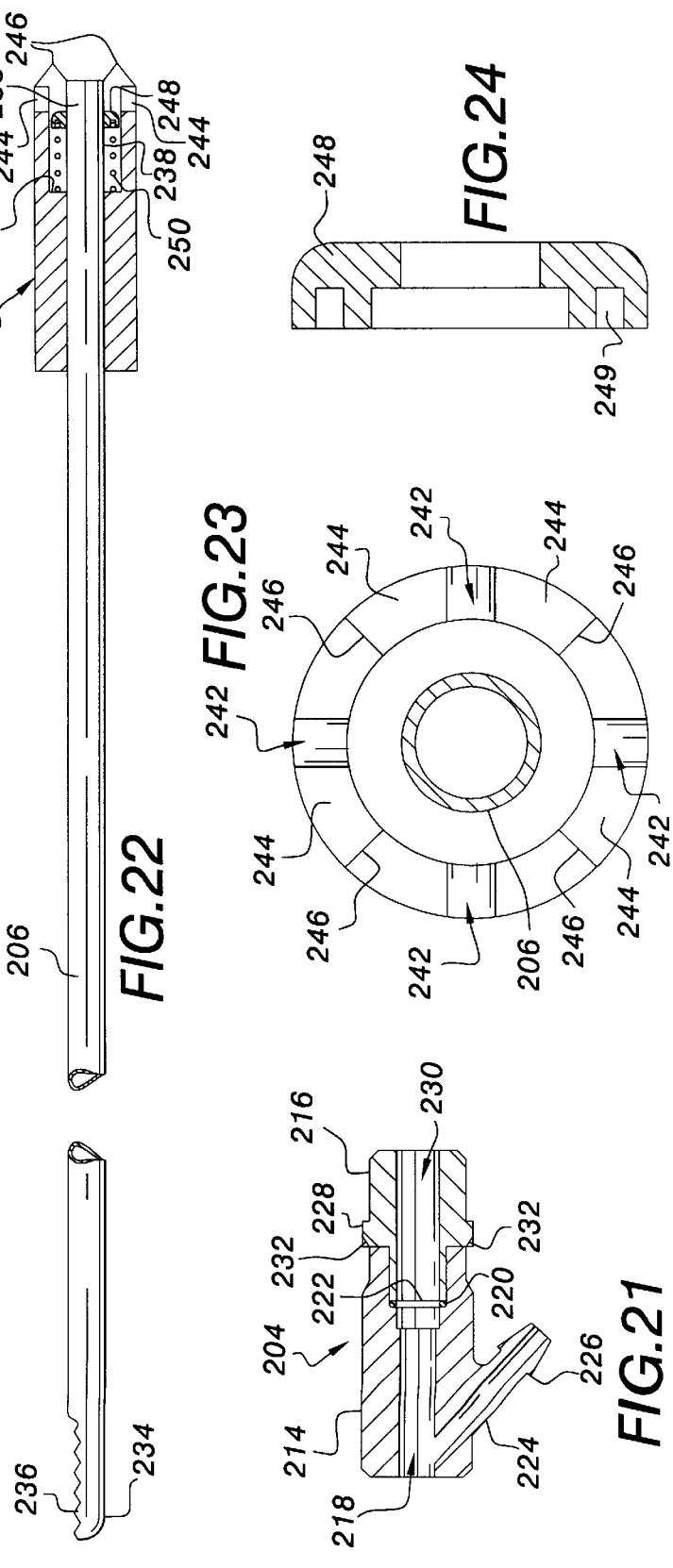

SURGICAL BLADES ASSEMBLY

CROSS-REFERENCE TO RELATED APPLICATION

This application is a divisional of pending application Ser. No. 08/775,147, filed Dec. 31, 1996, which is a continuation-in-part of pending application Ser. No. 08/719,130 filed Sep. 24, 1996, both now abandoned, the disclosures of the foregoing patent applications being is incorporated herein by reference.

BACKGROUND OF THE INVENTION

1. Field of the Invention

The present invention relates to powered handpieces for driving surgical blades and, more particularly, to electric motor driven, powered handpieces, surgical blade assemblies for use with such handpieces, powered handpiece systems utilizing non-sterile electric motors and methods for supplying powered handpieces for use in surgery.

2. Brief Description of the Prior Art

Powered handpieces are commonly used in many medical specialities to drive surgical blades for performing various diverse cutting functions including resection, comminution, dissection, debridement, shaving, drilling, pulverizing and shaping of anatomical tissue. In the areas of ENT/Head/Neck surgery, powered or motorized handpieces and systems have been proposed as illustrated by the Stryker Hummer system of Stryker Endoscopy, San Diego, Calif., the Apex System of Linvatec, Incorporated, Largo, Fla., the PS 3500 and EP-1 Surgical Drive System of Dyonics, Inc. of Andover, Mass. and the Wizard microdebrider system of Xomed, Inc., Jacksonville, Fla. Conventional powered handpieces are typically all metal and reusable in design with permanently installed motors. Such handpieces are typically decontaminated and sterilized for reuse by steam autoclave and/or soaking in a disinfectant solution resulting in reduced reliability and/or life of the motors due to the heating and cooling cycles and/or due to moisture seepage. A further disadvantage of conventional powered handpieces is that the motor of a handpiece cannot be replaced prior to surgery with a different speed motor in accordance with the procedure to be performed.

Conventional powered handpieces generally use suction to evacuate anatomical tissue cut or excised by the blades. Powered handpieces currently in use generally force the excised anatomical tissue to follow a suction path with major or substantial bends or angles. Accordingly, there is a tendency for the excised tissue to become clogged in the handpieces thusly impairing operation of the handpieces and compromising the surgical procedure.

Another drawback of some conventional powered handpieces is that the handpieces can only be operated by a power console specifically designed for the handpieces and not by a power consoles designed for other manufacturer's handpieces. Such handpieces therefore require a major investment in capital equipment for the associated power console.

SUMMARY OF THE INVENTION

Accordingly, it is a primary object of the present invention to overcome the disadvantages of prior art powered or motorized handpieces for driving surgical blades.

Another object of the present invention is to facilitate evacuation of cut or excised anatomical tissue from the cutting tip of a surgical blade and out of a powered handpiece for the blade.

A further object of the present invention is to avoid clogging of excised tissue evacuated through a suction channel of a powered handpiece for a surgical blade by reducing areas of turbulence in the suction channel.

A still further object of the present invention is to evacuate cut or excised anatomical tissue from a surgical blade through a suction channel extending through a powered handpiece for the blade, the suction channel having a portion extending through a drive shaft for rotatably driving the blade with the channel portion being parallel to a longitudinal axis of a motor in the handpiece.

An additional object of the present invention is to increase the reliability and/or life of an electric motor of a reusable powered handpiece by providing a method of supplying a powered handpiece for surgery including removing the electric motor from a body of the handpiece prior to medically acceptable sterilization of the handpiece body to medical standards and reinstalling the electric motor in the sterilized handpiece body prior to reuse of the handpiece.

The present invention has as a further object to utilize a non-sterile motor in a reusable powered handpiece by removing the non-sterile motor from a body of the handpiece prior to sterilization of the handpiece body to medical standards and reinstalling the non-sterile motor in the sterilized handpiece body subsequent to sterilization without contaminating the sterilized handpiece body.

The present invention has as an additional object to provide a device for installing a non-sterile motor in driving engagement with a drive unit in a sterile handpiece body without contaminating the sterile handpiece body.

Additionally, the present invention has as an object to provide a surgical blade assembly for use with a reusable powered handpiece having a non-sterile motor removable from a body of the handpiece prior to medically acceptable sterilization of the handpiece body to medical standards and reinstallable in the handpiece body subsequent to sterilization thereof.

Another object of the present invention is to provide a surgical blade assembly for use with a reusable powered handpiece having a suction channel extending through a drive shaft for rotatably driving the blade, the drive shaft being driven by a motor disposed parallel to the drive shaft.

Some of the advantages of the present invention are that diverse non-sterile, electric motors are readily interchangeable with the handpiece allowing an optimal motor to be selected in accordance with procedural use, the handpiece is relatively lightweight, compact and ergodynamically functional for use by surgeons in various specialities and, in particular, the areas of ENT/Head/Neck surgery, accurate alignment of the motor assembly with the drive unit is assured during installation of the motor assembly in the handpiece body, the motor assembly can be installed in the handpiece body by operating personnel just prior to the surgical case, the handpiece can be powered off of various conventional power consoles, and various diverse blades are interchangeable with the handpiece for performing various diverse functions.

These and other objects, advantages and benefits are realized with the present invention as characterized in a powered handpiece including a reusable handpiece body having a distal end for releasably receiving a surgical blade, a drive unit in the handpiece body including a drive shaft for driving the blade to cut anatomical tissue, a motor assembly for being disposed in the handpiece body for driving the drive unit and an electrical cord assembly for being electrically coupled between the motor and a power console. The handpiece body is capable of being medically sterilized to medical standards, such as by steam autoclave, gas sterilization and/or soaking, prior to each use. The motor assembly is removable from the handpiece body prior to sterilization of the handpiece body and is replaceable in the handpiece body subsequent to sterilization thereof without contaminating the sterile handpiece body. An installation device for inserting the motor assembly in the sterilized handpiece body without contaminating the sterilized handpiece body includes a funnel capable of being sterilized to medical standards and having a flared head and a tubular stem for being disposed over an open proximal end of the handpiece body. The motor assembly is inserted through the funnel into the open proximal end of the handpiece body without impairing the sterility of the handpiece body. In order to insure that the motor assembly is inserted in the handpiece body in driving engagement with the drive unit, an alignment mechanism is provided including a slot or keyway in the proximal end of the handpiece body and a protrusion or key on the motor assembly for being received in the slot; and, when the key of the motor assembly is received in the keyway of the handpiece body, the motor assembly will be in driving engagement with the drive unit. The funnel includes a protrusion or key for being received in the keyway of the handpiece when the funnel is disposed over the handpiece body. A notch is disposed in the funnel in longitudinal alignment with the key of the funnel and, therefore, with the keyway of the handpiece. The key of the motor assembly and the key of the funnel can be received simultaneously in the keyway such that the key of the motor assembly is passed through the notch into the keyway when being inserted through the funnel to insure proper alignment of the motor assembly with the drive unit. Once the motor assembly is properly installed in the handpiece body, the funnel is removed and the electrical cord assembly is coupled between the motor assembly and, therefore, the handpiece body, and a power console. The electrical cord assembly, which is capable of being sterilized to medical standards for reuse, includes a first plug for being electrically coupled with an electrical connector of the motor assembly and a second plug for being electrically coupled with a power console. The first plug carries a locking ring selectively movable into locking engagement with the proximal end of the handpiece body to secure the motor assembly therein. A surgical blade assembly for use with the powered handpiece according to the present invention includes an elongate outer tubular blade having a distal cutting end, a hub mounting a proximal end of the outer blade, an elongate inner tubular blade having a distal cutting end for cooperating with the cutting end of the outer blade to cut anatomical tissue, and a hub mounting a proximal end of the inner blade. The inner blade is concentrically disposed in the outer blade with the inner blade passing through the hub of the outer blade. The hubs of the outer and inner blades are releasably coupled with the distal end of the handpiece body with the inner blade in driving engagement with the drive shaft. The handpiece body includes a substantially straight suction channel for evacuating tissue cut by the blades through the handpiece body for external collection. The suction channel includes a portion extending through the drive shaft parallel to a longitudinal axis of the motor assembly.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 2 is an exploded view, partly in section, of the powered handpiece according to the present invention.

FIG. 3 is a side sectional view of a collet assembly of the powered handpiece.

FIG. 4 is a side sectional view of a transfer hub assembly of the powered handpiece.

FIG. 5 is a side view, partly in section, of a front drive shaft of a drive unit disposed in the transfer hub assembly.

FIG. 6 is a side view, partly in section, of a rear drive shaft of the drive unit.

FIG. 7 is a top view of the rear drive shaft.

FIG. 8 is a broken side view of a distal portion of a motor assembly of the handpiece.

FIG. 9 is a broken side view, partly in section, of a proximal portion of the motor assembly.

FIG. 10 is a side view of an electrical connector of the motor assembly.

FIG. 11 is a proximal end view of the electrical connector.

FIG. 12 is a distal end view of the electrical connector.

FIG. 13 is a broken side view, partly in section, of an electrical cable assembly of the powered handpiece connected between a body of the handpiece and a power console.

FIG. 14 is a broken perspective view of a plug of the electrical cable assembly for mating with the electrical connector.

FIG. 15 is a side sectional view of an installation device for installing the motor assembly in the body of the handpiece.

FIG. 16 is a rearward end view of the installation device.

FIG. 17 is a forward end view of the installation device.

FIG. 18 is a fragmentary view, partly in section, of the installation device.

FIG. 19 is a broken, exploded perspective view of the installation device.

FIG. 20 is a broken side view of a blade assembly for use with the powered handpiece according to the present invention.

FIG. 21 is a side sectional view of a hub of an outer blade of the blade assembly.

FIG. 22 is a broken side view, partly in section, of an inner blade and hub of the blade assembly.

FIG. 23 is an end view of the hub of the inner blade.

FIG. 24 is a side sectional view of a seal for the hub of the inner blade.

DESCRIPTION OF THE PREFERRED EMBODIMENT

Figure 1:
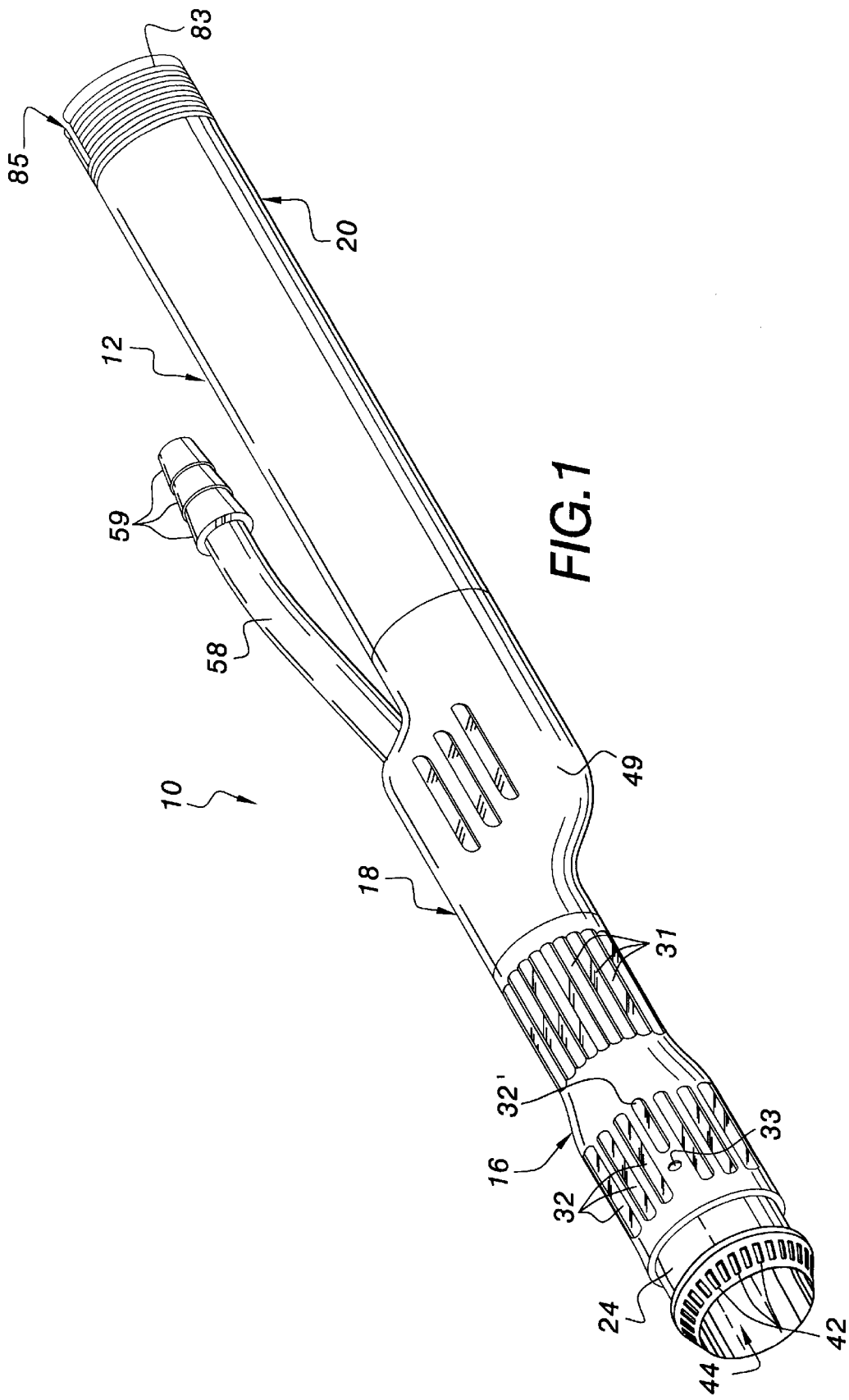
FIG. 1 is a perspective view of a powered handpiece according to the present invention.

A powered surgical handpiece 10 according to the present invention is illustrated in FIGS. 1 and 2 and includes a handpiece body 12 and a motor assembly 14 for being removably installed in handpiece body 12. The handpiece body 12 includes a collet assembly 16, a transfer hub assembly 18 and a motor enclosure 20. Collet assembly 16, as shown in FIG. 3, is designed to releasably couple a desired surgical blade to the handpiece body and includes an outer collet member 22, a middle collet member 24 and an inner collet member 26. Outer collet member 22, which is preferably made of stainless steel, is hollow and has a cylindrical rearward section 28 mounted to a forward end of transfer hub assembly 18 and a cylindrical forward section 30 extending distally from rearward section 28 in longitudinal or axial alignment therewith to terminate at a peripheral edge. Rearward section 28 has a uniform external diameter, smaller than a uniform external diameter of forward section 30, except for a distal portion of the rearward section 28 which is flared or of increasing external diameter in the distal direction to merge with the external diameter of the forward section 30. A plurality of longitudinally extending grooves or recesses 31 are formed in an external surface of the wall forming rearward section 28, the grooves 31 being of the same length and extending part way through the thickness of the rearward section wall. Grooves 31, which extend parallel to a longitudinal axis of the outer collet member 22, are juxtaposed to be laterally aligned with one another with little or no space between lateral or side edges of adjacent grooves 31 as shown in FIG. 1. A plurality of longitudinally extending grooves or recesses 32, similar to grooves 31, are formed in an external surface of the wall forming forward section 30 to extend part way through the thickness of the forward section wall. Grooves 32 extend parallel to the longitudinal axis of the outer collet member 22 and are juxtaposed to be laterally aligned with one another. The grooves 32 are laterally juxtaposed with a space between lateral or side edges of adjacent grooves 32 that is greater than the space between the side edges of grooves 31 as shown in FIG. 1. Grooves 32 are of the same length except for grooves 32', spaced 90° from one another about the longitudinal axis of outer collet member 22, which have a length less than the length of the remaining grooves 32. Set screws 33 are received in holes formed through the thickness of the forward section wall distally of and in longitudinal alignment with grooves 32', respectively, with the set screws 33 disposed proximally of distal ends of the remaining grooves 32. The grooves 31 and 32 have rounded distal and proximal ends and serve to facilitate grasping of the handpiece body 12. Outer collet member 22 has a lumen or internal passage extending entirely therethrough with the rearward section 28 defining a rearward passage section of uniform diameter or cross-section, and the forward section 30 defining a forward passage section of uniform diameter or cross-section larger than the diameter or cross-section of the rearward passage section. The rearward section wall is of increased thickness along the distal portion of the rearward section 28 to define an internal shoulder 34 extending transverse to the longitudinal axis of the outer collet member 22 at the junction of the rearward passage section with the forward passage section. The set screws 33 protrude inwardly into the forward passage section.

Middle collet member 24, which is preferably made of stainless steel, is hollow and includes a tubular stem 35 terminating proximally at an outwardly protruding, transverse flange 36 and includes a cylindrical front end 37 extending longitudinally, distally from the stem 35 in longitudinal or axial alignment therewith to terminate distally at a tapered nose 38. The external diameter of stem 35 is smaller than the external diameter of front end 37 such that an external, transverse shoulder 39 is formed at the junction of front end 37 with stem 35. The front end 37 and the flange 36 have the same external diameter, which is selected to be closely received in the forward section 30 of the outer collet member 22 while allowing the middle collet member 24 to move longitudinally relative to the outer collet member. Nose 38 defines an annular rim 40, larger in external diameter than front end 37, tapering to a transverse planar end wall 41. A plurality of radially extending grooves or recesses 42 are formed in the truncated conical external surface of nose 38 to facilitate grasping of the middle collet member 24. A lumen or internal passage extends entirely through the middle collet member 24 and includes a rearward passage segment of uniform diameter or cross-section extending through stem 35 and part way into front end 37, an intermediate passage segment of increasing diameter or cross-section extending distally from the rearward passage segment and a forward passage segment of uniform diameter or cross-section extending distally from the intermediate passage segment to terminate at an inner face of end wall 41. The forward, intermediate and rearward passage segments are longitudinally or axially aligned with one another, and the interior surface of the front end 37 is angled along the intermediate passage segment to define an internal sloping shoulder 43 between the forward and rearward passage segments. The end wall 41 has an opening or aperture 44 therein longitudinally or axially aligned with the internal passage of middle collet member 24 and establishing communication with the forward passage segment from externally of the handpiece body 12.

Inner collet member 26 is preferably made of stainless steel and comprises an elongate, hollow cylindrical or tubular member of uniform external diameter defined by a wall of uniform thickness along a distal portion of the cylindrical member and of uniform greater thickness along the remainder of the cylindrical member to form an internal transverse shoulder 45. A lumen or internal passage is defined entirely through the inner collet member 26 and includes a rearward passage portion of uniform diameter or cross-section and a forward passage portion of uniform diameter or cross-section, larger than the uniform diameter or cross-section of the rearward passage portion, with the shoulder 45 being disposed at the junction of the forward and rearward passage portions. A plurality of semi-spherical holes 46 are formed through the wall of the distal portion of the inner collet member 26 at 120° spaced locations about a longitudinal axis of the inner collet member 26 with the holes 46 communicating with the forward passage portion. A spherical ball bearing 47, is disposed in each hole 46 such that the ball bearings 47 protrude externally beyond an external surface of the inner collet member 26 and protrude internally beyond an internal surface of the inner collet member to protrude into the forward passage portion while being prevented from passing through the holes 46 into the forward passage portion. The inner collet member 26 has an external diameter or size to be closely received in the rearward passage section of the outer collet member 22 with the external surface of the inner collet member in contact with an internal surface of the outer collet member.

Middle collet member 24 is assembled to the outer collet member 22 in concentric or coaxial arrangement with stem 35 disposed in the forward passage section of the outer collet member 22 and flange 36 disposed proximally of set screws 33. The distance that set screws 33 protrude inwardly into the forward passage section of outer collet member 22 is the same as or slightly less than the height of external shoulder 39. The inner collet member 26 is concentrically or coaxially disposed in the outer collet member 22 with a proximal end of the inner collet member 26 fixedly secured, such as with adhesive, in rearward section 28 such that a distal end of the inner collet member 26 is disposed slightly distally of the distal peripheral edge of the outer collet member 22. A helical coil spring 48, preferably made of stainless steel, is concentrically disposed around the inner collet member 26 and is mounted in compression between internal shoulder 34 and flange 36 to bias the middle collet member 24 longitudinally, distally relative to the outer collet member 22 to an extended position as shown in FIGS. 2 and 3.

In the extended position, flange 36 is biased into abutment with set screws 33, and external shoulder 39 is disposed slightly proximally of the distal peripheral edge of outer collet member 22. There is a small circumferential gap or space between the external surface of the inner collet member 26 and an internal surface of stem 35 such that the protruding ball bearings 47 are in contact with the internal surface of stem 35 when the middle collet member 24 is in the extended position. Accordingly, the ball bearings 47 cannot move radially outwardly due to confinement by stem 35 and cannot move inwardly through the holes 46. The middle collet member 24 is movable longitudinally, proximally relative to the outer collet member 22 from the extended position to a retracted position wherein the external shoulder 39 abuts the set screws 33 which serve as a positive stop or abutment limiting proximal movement of the middle collet member 24 in the retracted position. In the retracted position, ball bearings 47 are no longer disposed in or aligned with stem 35 but, rather, are disposed in or aligned with the diametrically larger forward passage segment of front end 37 such that the ball bearings 47 can be moved radially outwardly by a hub of a surgical blade introduced in inner collet member 26 via aperture 44 as explained further below. Middle collet member 24 is movable from the retracted position back to the extended position due to the bias of spring 48 causing ball bearings 47 to again be held in place in the holes 47 of the inner collet member 26.

Transfer hub assembly 18 is best illustrated in FIG. 4 and includes a transfer body 49 mounted to the collet assembly 16 and a drive unit 50 disposed in the transfer body 49 for driving a surgical blade inserted in collet assembly 16. Transfer body 49 is preferably made of titanium or stainless steel and includes a distal cylindrical extension 51 and a proximal cylindrical extension 52 longitudinally and laterally offset from and not aligned with one another and a midsection 53 extending diagonally or angularly between the distal and proximal cylindrical extensions. A recess extends longitudinally in the distal extension 51 to terminate proximally at an end wall 54 in the midsection 53. A recess extends longitudinally in the proximal extension 52 to terminate distally at an end wall 55 in midsection 53, the end wall 55 being disposed distally of and parallel to end wall 54. The distal and proximal extension recesses are parallel to one another and are in communication with one another in midsection 53. A tubular neck 56 extends longitudinally, distally from the distal extension 51 in longitudinal or axial alignment therewith and has an external diameter, smaller than the external diameter of the distal extension, to be closely received in the rearward section 28 of the outer collet member 22 with a distal end of neck 56 in abutment with the proximal end of inner collet member 26 and with a proximal peripheral edge of the outer collet member 22 in abutment with an external transverse shoulder at the junction of neck 56 with distal extension 51. The neck 56 is fixedly secured to the outer collet member 22, such as adhesively, with the lumen or internal passage of neck 56 longitudinally or axially aligned with the internal passage of inner collet member 26. A passageway 57 in the mid-section 53 extends longitudinally, proximally from end wall 54 in communication with the recess of distal extension 51. Passageway 57 includes a forward passageway portion or part longitudinally or axially aligned with the recess of distal extension 51 and a rearward passageway portion or part having a longitudinal axis disposed at a minimal acute angle with a longitudinal axis of the forward passageway portion. According to a preferred embodiment, the longitudinal axis of the rearward passageway portion is disposed at an angle of 15° to the longitudinal axis of the forward passageway portion. The rearward passageway portion of passageway 57 has an outlet along an external surface of midsection 53 to establish communication with the passageway 57 from externally of the handpiece body 12. The rearward passageway portion of passageway 57 receives a distal end of a suction tube 58. Suction tube 58, which is preferably made of stainless steel, has a distal tube segment terminating distally at the distal end received in passageway 57 and a proximal tube segment terminating proximally at an open proximal end for being coupled with a standard suction canister. The distal end of the suction tube is secured in passageway 57, such as adhesively, with the distal end of the suction tube located at the junction of the forward passageway portion with the rearward passageway portion. The distal segment of tube 58 is longitudinally or axially aligned with the rearward passageway portion of passageway 57. The proximal segment of tube 58 is disposed parallel with the forward passageway portion of passageway 57 and has a plurality of truncated conical configured barbs 59 adjacent the open proximal end thereof for connection with the suction canister. As shown in FIG. 4, three barbs 59 of increasing diametric size are arranged on tube 58 in order of size with the diametrically smallest barb disposed closest to the open proximal end of the suction tube. The recess of proximal extension 52 has a uniform diameter forward recess section and a uniform diameter rearward recess section, larger in diameter than the forward recess section, longitudinally or axially aligned with one another. An internal, transverse shoulder 60 is disposed in the proximal extension 52 at the junction of the forward and rearward recess sections. The transfer body 49 can have a plurality of external oblong recesses as shown in FIG. 1, the recesses extending part way through the thickness of the wall of the transfer body to facilitate manual grasping or gripping of the transfer body during use.

Drive unit 50, also shown in FIG. 4, includes a front drive shaft 61 disposed in the recess of distal extension 51 and a rear drive shaft 62 disposed in the recess of proximal extension 52. Front drive shaft 61, shown in FIG. 5, carries or is formed with a gear 63 and has a first cylindrical portion of uniform external diameter extending distally from gear 63 and a second cylindrical portion of uniform external diameter, smaller than the external diameter of the first cylindrical portion, extending distally from the first cylindrical portion in longitudinal or axial alignment therewith. An external, transverse shoulder 64 is defined on the front drive shaft 61 at the junction of the first and second cylindrical portions. Gear 63 has an external diameter or size greater than the external diameter of the first cylindrical portion and has a plurality of gear teeth 65 parallel with a longitudinal axis of the front drive shaft 61. A longitudinal bore 66 is formed entirely through the front drive shaft 61 and includes a distal bore section of uniform diameter extending part way through the second cylindrical portion and a proximal bore section of uniform diameter, smaller than the diameter of the distal bore section, extending longitudinally, proximally from the distal bore section through the remainder of the front drive shaft 61. A proximally angled or sloping internal shoulder 67 is disposed in bore 66 at the junction of the distal and proximal bore sections. A pair of apertures are formed through the wall of the front drive shaft close to a distal end thereof, the apertures being disposed at 180° spaced locations about the longitudinal axis of front drive shaft 61 to receive drive pins 68, respectively. Pins 68 protrude externally in a radial direction from the front drive shaft 61 and have inner ends flush with an internal surface of the second cylindrical portion of the front drive shaft and rounded outer ends spaced from an external surface of the second cylindrical portion of drive shaft 61. The front drive shaft 61 including gear 63 is preferably made of stainless steel, and a proximal face of gear 63 is highly polished for smoothness.

Rear drive shaft 62, as illustrated in FIGS. 6 and 7, carries or is formed with a gear 69 and has a first cylindrical section of uniform external diameter extending proximally from gear 69 and a second cylindrical section of uniform external diameter, smaller than the external diameter of the first cylindrical section, extending proximally from the first cylindrical section in longitudinal or axial alignment therewith such that an external transverse shoulder 70 is defined at the junction of the first and second cylindrical sections. Gear 69 is similar to gear 63 and has a plurality of gear teeth 71 for mating with the gear teeth 65 in driving engagement. Rear drive shaft 62 has an open proximal end communicating with a longitudinal bore 72 extending distally from the open proximal end to terminate at a conical end surface in the second cylindrical section of the rear drive shaft. Opposed slots 73 are formed through the wall of the second cylindrical section of rear drive shaft 62 at 180° spaced locations about a longitudinal axis of the rear drive shaft. Slots 73 communicate with bore 72 and have open proximal ends communicating with the open proximal end of the rear drive shaft and arcuate distal edges disposed proximally of the conical end surface of bore 72. Slots 73 define a pair of opposed prongs 74 on rear drive shaft 62. Each slot 73 has a distal portion of substantially uniform width and an outwardly flared proximal portion of increasing width. Accordingly, each prong 74 terminates proximally at a triangular configured tip 75. Slots 73 have a width between parallel side edges of the prongs, and the width of the slots 73 is of a size to receive a drive pin of motor assembly 14 as explained further below. The parallel side edges of the prongs are parallel with the longitudinal axis of the rear drive shaft, and the walls forming the prongs are beveled interiorly along the tips 75. The rear drive shaft 62 including gear 69 is preferably made of stainless steel.

Front drive shaft 61 is disposed in the recess of the distal extension 51 of transfer body 49 with the proximal surface of gear 63 adjacent end wall 54 and with the front drive shaft extending into the neck 56 as shown in FIGS. 2 and 4. The bore 66 of front drive shaft 61 is axially aligned with the forward portion of passageway 57, which is disposed proximally of bore 66. A retaining ring 76, such as a stainless steel Smalley retaining ring of Smalley Steel Ring Co., Wheeling, Ill., is disposed on the second cylindrical portion of the front drive shaft 61 distally of external shoulder 64 and is secured in an internal groove or recess formed in the distal extension 51. A pair of radial shielded bearings 77 are mounted on the first cylindrical portion of front drive shaft 61, and a washer spring 78 is disposed around the front drive shaft 61 between retaining ring 76 and a distalmost bearing 77. A rotary seal 79 is disposed in. an annular groove or recess extending proximally a short distance from end wall 54 in communication with the distal extension recess. Seal 79 is a two-part seal including an O-ring 79A and an annular seal ring 79B disposed between the O-ring 79A and the proximal surface of gear 63. The O-ring and seal ring are made of compressible materials; and, preferably, the O-ring 79A is made of 5-148 EPR and the seal ring 79B is made of mineral filled PTFE. The gear 63 is pre-loaded against seal 79 such that the proximal surface of gear 63 is in direct contact with the seal ring 79B and does not contact the end wall 54. Accordingly, there is a small gap or space between the proximal of gear 63 and the end wall 54 to eliminate metal to metal contact.

The front drive shaft 61 is mounted for rotation within the transfer body 49 with the drive pins 68 disposed in neck 56 for being coupled with a hub of a hollow, tubular or cannulated surgical blade which is to be driven by the drive unit 50. When a blade is coupled to the front drive shaft 61, the lumen or hollow interior of the blade and its hub will be longitudinally or axially aligned with the bore 66 which, in turn, is longitudinally aligned with the forward portion of passageway 57 such that bore 66 and passageway 57 together define a continuous, substantially straight suction channel in the handpiece body disposed proximally of the blade for evacuating anatomical tissue cut by the blade from the handpiece body 12. The suction channel is substantially straight; that is, a substantial portion of the length of the suction channel is linear and coaxial with the blade. Only the rearward passageway portion of passageway 57, which accounts for a minimal portion of the length of the suction channel in the handpiece body is disposed at a minimal angle with the blade. The suction channel is therefore coaxial or linear with the blade from the blade up to the distal end of the suction tube 58. Accordingly, evacuation of tissue through the blade and the handpiece body is along a straight path up to the suction tube. Areas of turbulence in the suction channel are minimized such that the potential for evacuated material to become clogged within the handpiece is eliminated or greatly minimized.

As shown in FIGS. 2 and 4, rear drive shaft 62 is disposed in the recess of proximal extension 52 with a distal surface of gear 69 spaced slightly from end wall 55 and with teeth 71 in driving engagement with teeth 65. Prongs 74 are disposed in the rearward recess section of the proximal extension 52. A pair of radial shielded bearings 77' are mounted on the first cylindrical section of rear drive shaft 62. A retaining ring 76', similar to retaining ring 76, is disposed around the second cylindrical section of rear drive shaft 62 proximally of external shoulder 70 and is fixedly secured in an internal groove or recess formed in the proximal extension 52. A washer spring 78', similar to spring 78, is disposed around the rear drive shaft between a proximal most bearing 77' and the retaining ring 76'.

The motor enclosure 20 is preferably made of stainless steel or titanium and includes an elongate tubular member of uniform external diameter having a tubular neck 80 of smaller external diameter extending distally therefrom in longitudinal or axial alignment as shown in FIG. 2. An internal shoulder 81 and an external shoulder 82 are defined at the junction of neck 80 with the elongate tubular member. Neck 80 is received in the rearward recess section of proximal extension 52 with a distal end of neck 80 in abutment with the internal shoulder 60 of proximal extension 52 and with a proximal end of proximal extension 52 in abutment with the external shoulder 82 of motor enclosure 20. Neck 80 is secured to the transfer body 49, such as adhesively, and the prongs 74 of the rear drive shaft 62 are disposed within the neck 80 with tips 75 thereof disposed distally of internal shoulder 81. The motor enclosure 20 has an open proximal end circumscribed by a smaller diameter, annular proximal rim and has an external thread 83 extending distally from the proximal rim. The motor enclosure 20 is longitudinally or axially aligned with the rear drive shaft 62 allowing motor assembly 14 to be coupled with the rear drive shaft in driving engagement when the motor assembly is installed or inserted into the motor enclosure 20 via the open proximal end thereof. A slot or keyway 85, shown in FIG. 1, is formed in the proximal end of the motor enclosure 20 for receiving a key or protrusion of motor assembly 14 as explained further below. Keyway 85 has an oblong configuration with a central longitudinal axis parallel to the longitudinal axis of rear drive shaft 62. Keyway 85 has an open proximal end and an arcuate distal edge. Keyway 85 is aligned with the longitudinal axis of rear drive shaft 62; that is, longitudinal central axes of keyway 85 and rear drive shaft 62 are contained in the same plane and such plane contains the longitudinal axis of the motor enclosure 20.

Motor assembly 14, as shown in FIG. 2, includes an elongate, cylindrical motor housing 86, a motor 87, shown in FIG. 9, disposed within the housing 86 and an electrical connector 88 electrically connected with motor 87. Motor 87 includes a motor shaft 89 extending distally from a front end of motor housing 86 in longitudinal or axial alignment therewith. As shown in FIGS. 2 and 8, a pair of cylindrical drive pins 90 protrude from the motor shaft 89 in a radial direction at 180° spaced locations about a longitudinal axis of the motor shaft 89 for being received in slots 73 in driving engagement with prongs 74.

As shown in FIG. 9, the motor housing 86 has a diametrically enlarged, open rear end with an internal thread for threaded connection to connector 88. Motor 87 is preferably a three-phase, brushless, DC motor having Hall Effect sensors, such as that of Harowe Servo Controls, Inc. of West Chester, Penn.

The electrical connector 88 is illustrated in FIGS. 10–12 and includes a backshell 91 having a cylindrical main body portion and an externally threaded neck of smaller diameter extending distally from the main body portion. The externally threaded neck has an external size to be threadedly received by the internally threaded rear end of the motor housing 86 as shown in FIG. 9. The main body portion of backshell 91 has an external diameter or size that is the same or substantially the same as the external diameter or size of the rear end of motor housing 86 such that the backshell is diametrically flush with the motor housing. A raised key or protrusion 92 protrudes externally from the main body portion of backshell 91, the key 92 extending longitudinally, distally from a proximal peripheral edge of backshell 91. Key 92 has a configuration and size to mate with keyway 85 of motor enclosure 20; however, the height of key 92 is less than the height of keyway 85 to allow a key of an installation device to be received in keyway 85 simultaneously with key 92 as explained further below. A longitudinal axis of key 92 is disposed transverse or perpendicular to a common longitudinal axis of drive pins 90 such that the drive pins 90 are aligned with slots 73 when key 92 is aligned with keyway 85. Accordingly, key 92 and keyway 85 comprise an alignment mechanism for ensuring proper alignment of the motor assembly in the handpiece body. A cylindrical recess 93 is formed in the main body of backshell 91, the recess 93 extending distally from the proximal peripheral edge of the backshell to terminate at a base wall 94 in the backshell main body. A semi-cylindrical polarizing insert 95 is disposed in recess 93, the insert 95 extending proximally from base wall 94 to terminate at a planar surface flush with the proximal peripheral edge of the backshell main body portion. Insert 95 has a diameter smaller than the diameter of recess 93, and the insert 95 is disposed in the recess 93 with its diameter aligned with the diameter of recess 93. Accordingly, there is a semi-circumferential gap or space between a curved outer surface of insert 95 and a curved inner surface of the wall forming the backshell main body portion. A plurality of contacts 96 are mounted in the backshell 91 and have distal ends protruding longitudinally, distally from a forward surface of the backshell neck. Some of the contacts 96 extend longitudinally through the backshell 91 to terminate at proximal ends forming pins 97, and the remaining contacts 96 extend longitudinally through the backshell to terminate at proximal ends forming receptacles 98 to provide a male/female connector. As shown in FIG. 12, ten contacts 96 are arranged in the backshell 91 with five of the contacts 96 forming receptacles 98 in polarizing insert 95, and the remaining five contacts 96 forming pins 97 protruding proximally from base wall 94. Pins 97 are disposed in recess 93 in symmetrical or mirror image arrangement with receptacles 98. The distal ends of contacts 96 are designed, such as with slots, to be soldered to wire leads 99 of motor 87 as shown in FIG. 9. The pins 97 and receptacles 98 are designed to accept a polarized plug of an electrical cord assembly for connection to a power console for supplying electricity to motor 87 as explained further below. According to a preferred embodiment, connector 88 is a custom ERY-2C electrical connector of LEMO USA.

The handpiece body 12 is preferably made of durable, medically acceptable materials, such as stainless steel or hard coat anodized aluminum or titanium, for example, capable of being sterilized to medical standards, such as by steam or flash autoclaving, gas sterilization and/or soaking in a disinfectant solution. Accordingly, the handpiece body 12 is designed for repeated use. The motor assembly 14 is removably installed in handpiece body 12 allowing the motor assembly 14 to be removed from the handpiece body 12 prior to sterilization of the handpiece body and to be reinstalled in the sterilized handpiece body 12 prior to use. The motor assembly 14 can be non-sterile such that the motor assembly is not subjected to sterilization procedures that would reduce the reliability and/or life of the motor. According to a sterile transfer method of the present invention, a non-sterile motor assembly 14 is installed in the sterile handpiece body 12 without contaminating the sterile handpiece body as explained below.

The motor assembly 14 is installed in the handpiece body 12 with the key 92 of connector 88 disposed in the keyway 85 of motor enclosure 20. Accordingly, the drive pins 90 will be disposed in the slots 73 in driving engagement with prongs 74. The front end of motor housing 86 will be in abutment with the internal shoulder 81 of the motor enclosure 20 and the connector backshell 91 will be flush with the proximal rim of the motor enclosure 20.

The motor 87 is powered by a software controlled power console via an electrical cord assembly 111 coupled with connector 88 and the power console as shown in FIG. 13. Cord assembly 111 comprises a length of shielded electrical cable or cord 113 having a first end carrying a first plug 115 for being coupled with electrical connector 88 and having a second end carrying a second plug P for being coupled to the power console. Cable 113 can be designed in many various ways and can include various types of shielded electric cable, such as that of W.L. Gore & Associates, Inc. of Phoenix, Ariz., having conductors for transmitting electricity from the power console PC to the motor 87. As shown in FIG. 14, plug 115 is designed as a male/female plug for being coupled with electrical connector 88 and has a cylindrical forward end with a planar end surface 117 for abutting base wall 94 of connector 88. A polarizing recess 119 corresponding to polarizing insert 95 is formed in the plug 115. A plurality of receptacles 121 are disposed in the plug 115 corresponding to pins 97 of electrical connector 88, and a plurality of pins 123 are disposed in the polarizing recess 119 corresponding to receptacles 98 of connector 88, the receptacles 121 and pins 123 being electrically connected with conductors of cable 113. Accordingly, the plug 115 can be plugged into the electrical connector 88 with the polarizing insert 95 of the connector received within the polarizing recess 119 of the plug with the pins 97 of the connector disposed within the receptacles 121 of the plug and the pins 123 of the plug disposed within the receptacles 98 of the connector. As shown in FIGS. 13 and 14, a locking or retaining ring 125 is concentrically disposed over the plug 115 and has an internal annular protrusion 127 disposed proximally of an annular abutment 129 of plug 115. The locking ring carries an internal seal 184 disposed proximally of protrusion 127 to keep out moisture. The locking ring 125, which is movable longitudinally relative to plug 115, is rotatable relative to plug 115 and is internally threaded along a distal end thereof for threaded engagement with the thread 83 of motor enclosure 20. Accordingly, a circumferential or annular gap or space is disposed between plug 115 and locking ring 125 for accommodating the proximal end of the motor enclosure 20 when the locking ring is threaded thereon. The cord assembly 111 is designed and constructed to be sterilized, such as via steam autoclave, for example, to medical standards for repeated use.

FIGS. 15–17 illustrate a reusable motor installation device 100 for use in the sterile transfer method according to the present invention. Motor installation device 100 is in the nature of a funnel 100 including a flared or truncated conical head 102 having a relatively wide inlet end and a relatively narrow outlet end opposite the inlet end and a tubular neck 103 extending longitudinally, centrally from the head 102 in communication with the outlet end. The wall forming head 102 is exteriorly beveled or angled at the junction of the head 102 with the tubular neck 103 to define a planar end surface 104 parallel to a plane containing a terminal circumferential or peripheral edge 105 at the inlet end of head 102. The tubular neck 103 is concentrically arranged with the head 102 and extends longitudinally therefrom to terminate at an open, free end that is externally threaded or ribbed as shown at 106 in FIG. 15. A circumferential lip 107 is disposed at the junction of head 102 with the neck 103, i.e. at the outlet end of head 102, and a notch 108 is formed in the lip 107 such that the lip is circumferentially broken or discontinuous. The lip 107 protrudes inwardly such that the outlet defined by lip 107 at the outlet end of head 102 is diametrically or circumferentially smaller than the lumen of neck 103. A key or protrusion, such as a dowel pin 109 extends through the wall forming the neck in longitudinal alignment with the notch 108. The key 109 is spaced longitudinally from the notch 108 and protrudes into the lumen of neck 103. The distance that key 109 protrudes into the neck 103 is selected to allow keys 92 and 109 to be disposed in the keyway 85 simultaneously when the motor assembly 14 is inserted into the handpiece body 12 through funnel 100 according to the sterile transfer method explained further below. The distance that key 109 is spaced longitudinally from seal 107 is selected such that the key 109 is disposed in the keyway 85 with the annular proximal rim of the motor enclosure 20 in abutment with lip 107 when the funnel is placed over the motor enclosure to install the motor assembly.

The neck 103 has a plurality of slots 101 formed therein, the slots 101 being equally spaced about a longitudinal axis of funnel 100. As shown in FIG. 18, four slots 101 are separated from one another by triangular shaped bridge segments 110 of neck 103. As shown in FIG. 15, slots 101 are spaced longitudinally from key 109, the slots 101 being disposed between key 109 and the open free end of neck 103. As shown in FIG. 19, a deformable O-ring 112 is positioned externally over neck 103 to be received in slots 101. When the O-ring is received in slots 101 as shown in FIGS. 15, 16 and 17, the O-ring is deformed to assume a somewhat square configuration with segments 114 of the O-ring protruding into the lumen of neck 103. Funnel 100 is made of a suitable medically acceptable material, such as titanium or stainless steel, and is capable of being sterilized along with O-ring 112 assembled thereon, such as by flash autoclaving, gas sterilization and/or soaking to medical standards for repeated use.

Prior to use, the funnel 100, electrical cord assembly 111 and the handpiece body 12, without the motor assembly 14 received in the motor enclosure 20, are medically sterilized such as via flash autoclaving, gas sterilization and/or soaking. The thusly sterilized components are handled by sterile operating personnel in a sterile operating field prior to surgery. According to the sterile transfer method, the handpiece body 12 is held with the open proximal end of motor enclosure 20 facing upwardly, and the neck 103 of funnel 100 is placed over the open proximal end of the motor enclosure 20. The funnel 100 is rotated relative to the motor enclosure 20 until the key 109 is aligned with the keyway 85. The key 109 will then drop into the keyway 85 until the proximal rim of the motor enclosure 20 is in abutment with the lip 107. The O-ring segments 114 grip the handpiece body 12 and resist removal of the funnel 100 from the handpiece body such that the funnel remains in place on the handpiece body even if the handpiece body is turned upside down. Accordingly, the funnel 100 will be locked in place on the handpiece body 12 with the key 109 protruding part way into the keyway 85. The non-sterile motor assembly 14, which is handled separately by operating personnel who can be non-sterile, is inserted, shaft end first, through the inlet end of funnel 100 and is rotated until the key 92 on the electrical connector 88 is aligned with the notch 108 in the lip 107. Accordingly, the key 92 will be aligned with the keyway 85, and the motor assembly 14 will pass through the neck of funnel 100 into motor enclosure 20 since the key 92 passes through the notch 108 and enters the keyway 85. The drive pins 90 will enter the slots 73 in driving engagement with prongs 74, the triangular shaped tips 75 of the prongs 74 providing a self-centering function to facilitate entry of the drive pins 90 in the slots 73. The funnel 100 is then manually withdrawn or removed from the handpiece body 12, overcoming the gripping force of O-ring 112 such that the key 109 is withdrawn from the keyway 85. The motor assembly 14 is now properly installed within the handpiece body 12 without compromising the sterility of the handpiece body.

Once the motor assembly 14 has been properly installed in the handpiece body 12, the sterile plug 115 is plugged into the electrical connector 88 with a press fit with the locking ring 125 disposed in a proximal longitudinal position relative to plug 115 to allow the polarizing insert 95 to enter the polarizing recess 119 causing pins 97 of the electrical connector to enter the receptacles 121 of the plug and causing the pins 123 of the plug to enter the receptacles 98 of the connector. The locking ring 125 is then rotated in a first rotational direction relative to the plug 115 to threadedly engage the proximal end of the motor enclosure 20. As the locking ring 125 is threaded over the proximal end of the motor enclosure, the locking ring is moved longitudinally, distally relative to the plug 115 to a distal longitudinal position. The locking ring is rotated and, therefore, is moved longitudinally until the threads of the locking ring and the motor enclosure, respectively, are fully engaged. The proximal end of the motor enclosure 20 is then held between the plug 115 and the locking ring 125, with the locking ring 125 preventing withdrawal of the plug 115 from the connector 88 and, therefore, preventing withdrawal of the motor assembly 14 from the handpiece body 12. The plug P is plugged into the power console, which is utilized to supply electric power to motor 87 to rotate motor shaft 89, operation of the console being controlled by the surgeon such as via a foot switch or pedal for the console or directly from the console. Motor shaft 89 rotates rear drive shaft 62 which in turn rotates front drive shaft 61 via gears 63 and 69. Front drive shaft 61 in turn rotates a surgical blade drivingly engaged therewith to cut anatomical tissue. The front drive shaft 61 can be rotated via the motor assembly for full rotational movement along 360° continuously in the same direction and/or for oscillatory rotational movement in reverse directions along less than 360°.

FIG. 20 illustrates a surgical blade assembly 200 for use with the handpiece 10. Blade assembly 200 includes an outer blade 202, a hub 204 mounting a proximal end of the outer blade, an inner blade 206 for being disposed in the outer blade with the inner blade passing through hub 204, and a hub 208 mounting a proximal end of the inner blade. Outer blade 202 includes an elongate tubular member having an open proximal end and an open distal end or tip 210 carrying a cutting edge 212. As shown in FIG. 21, hub 204 for outer blade 202 includes a forward hub part 214 and a rearward hub part 216. Forward hub part 214 includes a distal cylindrical main body portion tapering to a smaller external diameter proximal cylindrical portion. A longitudinal passage 218 extends entirely through the forward hub part 214 and includes a forward passage section of uniform diameter, an intermediate passage section of uniform diameter greater than the diameter of the forward passage section, and a rearward passage section of uniform diameter greater than the diameter of the intermediate passage section. An internal transverse shoulder 220 is defined at the junction of the intermediate and rearward passage sections, and an annular seal 222 is disposed in the passage 218 in abutment with shoulder 220. An angular extension 224 protrudes angularly, proximally from the forward hub part 214 and has a longitudinal passage extending entirely therethrough in communication with the passage 218. Extension 224 has an open free end formed with a barb 226 for being coupled with an irrigation supply tube. Rearward hub part 216 includes a distal cylindrical section, a proximal cylindrical section having an external diameter greater than the diameter of the distal cylindrical section and an annular flange 228 disposed between the distal and proximal cylindrical sections. A longitudinal passage 230 of uniform diameter extends entirely through the rearward hub part 216. A plurality of partial spherical recesses 232 are formed along an outer forward edge or corner of flange 228 at 30° spaced locations about a longitudinal axis of rearward hub part 216. The rearward hub part 216 is assembled to the forward hub part 214 with the distal cylindrical section of the rearward hub 216 part secured in the rearward passage section of the forward hub part 214 with a distal end of the rearward hub part 216 in abutment with seal 222. The distal section of the rearward hub part can be secured in the rearward passage section of the forward hub part in many various ways, such as adhesively. With the rearward hub part 216 assembled to the forward hub part, the passages 218 and 230 are longitudinally or axially aligned to form a continuous longitudinal passage through hub 204. The open proximal end of the outer blade 202 is secured, such as adhesively, in the forward passage section of the forward hub part 214 with the lumen or internal passage of the outer blade 202 longitudinally or axially aligned with the passage through hub 204. A hole or aperture is formed in the outer blade 202 in alignment with the longitudinal passage of angular extension 224 to establish communication between the passage of the angular extension and the lumen of outer blade 202.

Inner blade 206 is illustrated in FIG. 22 and includes an elongate tubular member having an open proximal end 233 and an open distal end or tip 234 carrying a cutting edge 236 designed to cooperate with cutting edge 212 to cut anatomical tissue. Hub 208 for inner blade 206 includes a cylindrical body having a passage 238 extending longitudinally entirely therethrough. Passage 238 has a forward passage portion and a rearward passage portion larger in diameter than the forward passage portion. An internal transverse shoulder 240 is defined at the junction of the forward and rearward passage portions. As shown in FIGS. 22 and 23, a plurality of oblong slots 242 are formed in a proximal end of hub 208 at 90° spaced locations about a longitudinal axis of hub 208 with the slots 242 extending longitudinally, parallel to the longitudinal axis of hub 208 to define prongs 244. Each slot 242 has a distal portion of uniform width and a proximal portion of increasing width in the proximal direction. Accordingly, the proximal portions of slots 242 flare out from the distal portions thereof such that the prongs 244 have triangular shaped tips 246, the prongs 244 being similar to the prongs 74. The hub 208 and the prongs 244 are designed to be disposed in the handpiece 10 with the drive pins 68 of the front drive shaft 61 disposed in a pair of opposed slots 242 in driving engagement with prongs 244. An annular or cylindrical seal member 248 is disposed within passage 238 at a proximal end of groove 249 along a forward surface thereof. A coil spring 250 is concentrically disposed in passage 238 and is mounted in compression between shoulder 240 and seal 248 with an end of the spring 250 being disposed in the groove 249. The open proximal end 233 of the inner blade 206 is disposed in the passage 238 to terminate proximally of seal member 248 and is secured, such as adhesively, in passage 238 with the inner blade passing concentrically through spring 250. Preferably, the blades are made of stainless steel and the hubs are made of plastic, such as ABS resin, for disposability or single patient use. The outer blade 202 is assembled with the inner blade 206 as shown in FIG. 20 with the inner blade 206 passing through hub 204 to align the cutting edges 212 and 236 and with hub 208 disposed proximally of hub 204. The inner blade 206 is of a size to be closely received within outer blade 202 and hub 204 while allowing the inner blade to be rotated relative to the outer blade to move the cutting edge 236 past the cutting edge 212 to cut anatomical tissue. The blade assembly 200 is coupled with the handpiece 10 by moving the middle collet member 24 longitudinally, proximally relative to the outer collet member 22 to the retracted position causing ball bearings 47 to be aligned with the forward passage segment of the middle collet member. The hubs 204 and 208 are introduced through the aperture 44 in the middle collet member 24 and are moved longitudinally to enter the passage of the inner collet member 26 such that the drive pins 68 of the front drive shaft 61 enter the slots 242 of hub 208, the triangular tips 246 of prongs 244 providing a self-centering function facilitating entry of the drive pins 68 into a pair of opposed slots 242. Flange 228 enters the passage of the inner col let member 26, causing the ball bearings 47 to be moved outwardly from holes 46.

With the hubs 204 and 208 fully inserted in the handpiece 10, a proximal surface of flange 228 will be in abutment with internal shoulder 45, and the partial spherical recesses 232 will be in alignment with holes 46. The middle collet member 24 is released, causing the middle collet member to be returned to the extended position due to the bias of spring 48. Return of the middle collet member to the extended position causes the ball bearings 47 to be moved inwardly into holes 46 and the partial spherical recesses 232 aligned therewith. Accordingly, flange 228 of hub 204 is prevented from moving distally and rotationally by ball bearings 47 and is therefore locked in place within the handpiece 10. The hub 208 cannot enter the rearward hub 204; and, accordingly, the hub 208 is also locked in place within the handpiece 10. The extension 224 of hub 204 is connected with an irrigation supply tube for supplying irrigation fluid between the outer blade and the inner blade, the seal 222 preventing egress of irrigation fluid proximally therepast. The spring biased seal 248 member of hub 208 allows some tolerance between the hub 208 and the front drive shaft 61 to maintain proper alignment therewith. Preferably, the blade assembly is provided in a sterile condition for single patient use and; since the seals 222 and 248 are disposed in the hubs 204 and 208, respectively, and not in the handpiece, they are not subjected to the rigors of medical resterilization. With the blade assembly 200 coupled with the handpiece 10, rotation of the front drive shaft 61, as controlled by the power console, causes the inner blade 206 to be rotated within and relative to the outer blade 202 to move cutting edge 236 past cutting edge 212 to cut anatomical tissue through the open distal ends of the blades. Irrigating fluid is supplied at the cutting tips 210 and 234 via extension 224 and the lumen of outer blade 202, such fluid passing through the hole or aperture in the outer blade to flow between the inner and outer blades. Anatomical tissue cut by the blades will be aspirated or evacuated through the inner blade member 206 and the handpiece 10 for collection in the suction canister coupled with suction tube 58. The seal 79 prevents material being evacuated from crossing the seal to gears 63 and 69.

Figure 25:
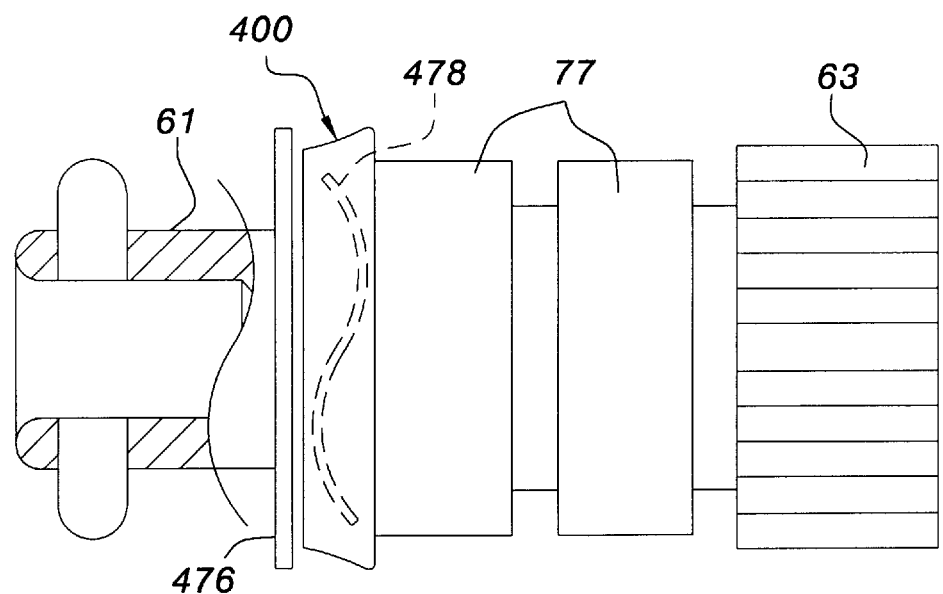
FIG. 25 is a sectional view of an alternative seal for the drive unit of the powered handpiece.
Figure 26:
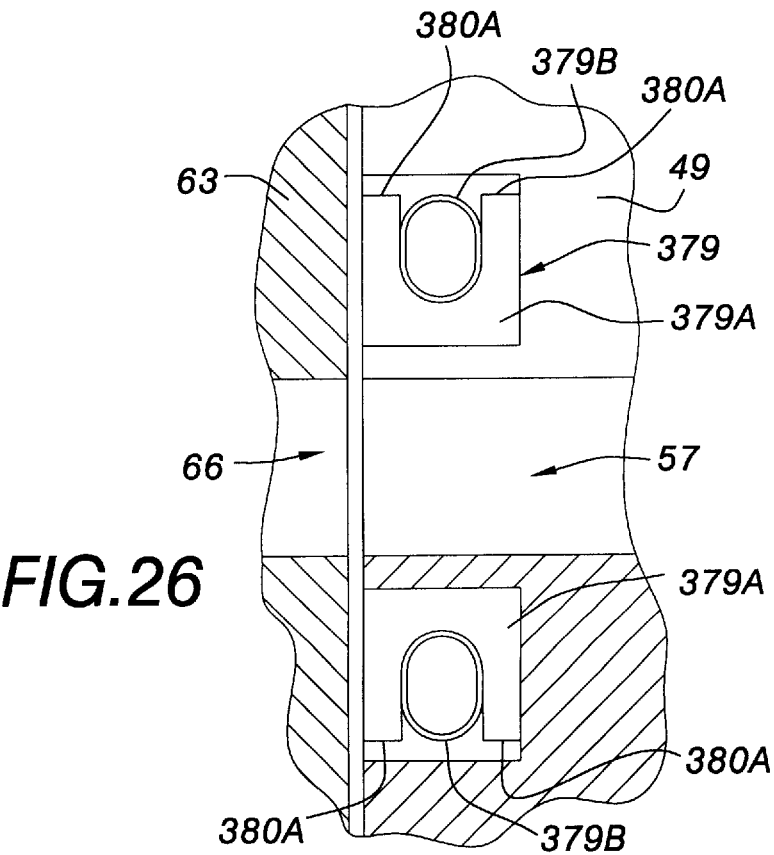
FIG. 26 is a side view, partly in section, illustrating a lip seal for the drive unit of the powered handpiece.

FIG. 25 illustrates at 379 an alternative seal forming a seal with the proximal surface of the gear of the front drive shaft. Seal 379 is disposed in an annular groove or recess of transfer body 49 and includes an annular seal member 379A having a U-shaped configuration in cross-section with spaced legs 380A and an annular spring 379B disposed between legs 380A. The space between legs 380A is disposed along an outer periphery of the seal member 379A to receive spring 379B, which has an oblong configuration in cross-section. A forward surface of seal member 379A is in contact with the proximal surface of gear 63 such that there is a small air gap between the proximal surface of the gear and the transfer body 49. Seal 379 functions similar to seal 79 in that the gear 63 is in contact with the seal member 379A and does not contact the transfer body 49, and the seal 379 prevents material evacuated from the handpiece from moving therepast.

FIG. 25 illustrates a lip seal 400 for use on the front and rear drive shafts. Lip seal 400 includes an annular seal member or ring, preferably made of compressible, deformable material, disposed around front drive shaft 61 between retaining ring 76 and bearings 77. Seal 400 has a slightly protruding proximal peripheral edge adjacent the distalmost bearing 77. Seal 400 can be used in place of the washer spring, or the seal 400 can be used in conjunction with a spring, such as a garter spring, a spring being shown within the seal 400 in dotted lines at 478. Although the seal 400 is illustrated on the front drive shaft 61, it should be appreciated that a seal 400 can be disposed on the rear drive shaft between the retaining ring and the proximalmost bearing in the same manner as described for the front drive shaft 61.

The handpiece of the present invention is relatively small and lightweight providing many functional benefits for the ENT surgeon as well as other medical specialities. The handpiece can be used with many various interchangeable blades having different cutting tips in accordance with a procedure to be performed. Tissue cut by the blades is evacuated through the handpiece in a substantially in-line or straight path while maintaining a small profile for the handpiece. Since tissue is evacuated along a straight path through the handpiece up to the suction tube, which itself is at a minimal angle, areas of turbulence in the suction channel are reduced such that clogging of tissue in the handpiece body is eliminated or greatly minimized. The reliability and/or life of the motor assembly is greatly increased since the motor assembly is removed prior to sterilization of the handpiece body for reuse and is reinstalled in the sterilized handpiece body prior to surgery without contaminating the handpiece body. Removability of the motor assembly allows various different motor assemblies with different operating speeds and features to be installed in the handpiece in accordance with optimal procedural use. The handpiece according to the present invention can be powered off of its own power console or the existing power consoles of various manufacturers by orienting the output signals of the power consoles for compatibility with the handpiece or by utilizing a motor assembly and/or cord assembly compatible with the power consoles.

Other objects and advantages of the present invention will become apparent from the following description of the preferred embodiments taken in conjunction with the accompanying drawings, wherein like parts in each of the several figures are identified by the same reference characters.

What is claimed is:

1. A surgical blade assembly in combination with a powered surgical handpiece, said powered surgical handpiece including a reusable handpiece body capable of being sterilized to medical standards prior to each use, a drive unit in said handpiece body including a drive shaft and a removable non-sterile motor installed in said handpiece body to rotatably drive said drive shaft, said motor being removable from said handpiece body prior to sterilization of said handpiece body and being reinstallable in said handpiece body subsequent to sterilization of said handpiece body and without contamination of said handpiece body by said motor, said surgical blade assembly including an elongate, tubular outer blade having an open distal end for receiving anatomical tissue therein, an open proximal end releasably coupled with said handpiece body and a lumen between said distal and proximal ends of said outer blade, a hub mounting said proximal end of said outer blade, an elongate, tubular inner blade concentrically, rotatably disposed in said outer blade with said inner blade passing through said hub and having an open distal end carrying a cutting edge for cooperating with said open distal end of said outer blade to cut anatomical tissue and an open proximal end releasably coupled to said drive shaft in driving engagement therewith and a hub mounting said proximal end of said inner blade, said hub of said inner blade having a longitudinal passage extending entirely therethrough in which said proximal end of said inner blade is disposed, said hubs being releasably secured in said handpiece body to mount said inner blade for rotation relative to said outer blade when said inner blade is rotatable driven by said drive shaft.

2. A surgical blade assembly in combination with a powered surgical handpiece as recited in claim 1 wherein said hub of said outer blade includes an irrigation supply passage communicating with said lumen of said outer blade for supplying irrigation fluid to said distal ends of said outer and inner blades, a longitudinal passage extending entirely therethrough in which said inner blade is disposed, and a seal disposed in said passage of said hub of said outer blade proximally of said irrigation supply passage for preventing passage of irrigation fluid proximally from said passage of said hub of said outer blade.

3. A surgical blade assembly in combination with a powered surgical handpiece as recited in claim 2 wherein said drive shaft has drive pins thereon and said hub of said inner blade is configured with slots for receiving said drive pins in driving engagement.

4. A surgical blade assembly in combination with a powered surgical handpiece as recited in claim 3 wherein said hub of said inner blade is configured with longitudinally extending prongs disposed between said slots, said prongs having tapered tips to center said inner blade relative to said drive shaft to facilitate insertion of said drive pins in said slots.

5. A surgical blade assembly in combination with a powered surgical handpiece as recited in claim 4 and further comprising a seal member disposed in said passage of said hub of said inner blade distally of said prongs and a spring in said passage of said hub of said inner blade biasing said seal member for providing longitudinal tolerance between said inner blade and said drive shaft.

6. A surgical blade assembly in combination with a powered surgical handpiece as recited in claim 5 wherein said prongs have triangular shaped tips.

7. A surgical blade assembly in combination with a powered surgical handpiece as recited in claim 6 wherein said outer blade has a central longitudinal axis, said handpiece body has a plurality of spherical ball bearings retained therein and said hub of said outer blade includes an enlarged, external annular flange having a plurality of partial spherical recesses therein at spaced locations about said central longitudinal axis for receiving said spherical ball bearings to releasably, lockingly secure said hub of said outer blade to said handpiece body.

8. A surgical blade assembly in combination with a powered surgical handpiece, said powered surgical handpiece including a reusable handpiece body having a collet assembly releasably coupling said blade assembly to said handpiece body, a drive unit in said handpiece body including a rotatable drive shaft, a motor assembly in said handpiece body including a longitudinal axis and a motor for driving said drive shaft and a suction channel in said handpiece body for evacuating tissue cut by said blade assembly and including a portion extending through said drive shaft parallel to said longitudinal axis of said motor assembly, said surgical blade assembly comprising an elongate outer tubular blade having a distal cutting end and having a proximal end and an elongate inner tubular blade disposed in said outer blade and having a distal cutting end for cooperating with said distal cutting end of said outer blade to cut anatomical tissue and having a proximal end, a hub at said proximal end of said outer blade receiving said inner blade therethrough and a hub at said proximal end of said inner blade, said hub of said outer blade being disposed in said handpiece body in releasable locking engagement with said collet assembly to position said hub of said inner blade in driving engagement with said drive shaft, said inner blade being rotatable relative to said outer blade by said drive shaft to cut anatomical tissue at said distal ends of said inner and outer blades.

9. A surgical blade assembly in combination with a powered surgical handpiece as recited in claim 8 wherein said inner blade is axially aligned with said portion of said suction channel when said inner blade is in driving engagement with said drive shaft.

10. A surgical blade assembly in combination with a powered surgical handpiece as recited in claim 9 wherein said distal cutting end of said inner blade includes a cutting edge having a plurality of cutting teeth.

11. A surgical blade assembly in combination with a powered surgical handpiece as recited in claim 10 wherein said distal cutting end of said outer blade includes a straight cutting edge.

12. A surgical blade assembly in combination with a powered surgical handpiece as recited in claim 10 wherein said distal cutting end of said outer blade includes a cutting edge having a plurality of cutting teeth.

* * * * *